(12) United States Patent
Hargreaves (10) Patent No.: US 7,129,046 B2
(45) Date of Patent: *Oct. 31, 2006

(54) LINKING TO CHEMICAL ARRAY ASSEMBLIES WITH METAL LAYERS

(75) Inventor: John S. Hargreaves, Mountain View, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 574 days.

This patent is subject to a terminal disclaimer.

(21) Appl. No.: 10/277,925

(22) Filed: Oct. 21, 2002

(65) Prior Publication Data

US 2004/0076963 A1 Apr. 22, 2004

(51) Int. Cl.
*C12Q 1/68* (2006.01)
*C07H 21/04* (2006.01)

(52) U.S. Cl. .......... 435/6; 435/287.2; 435/7.1; 435/174; 435/283.1; 536/23.1; 536/25.3

(58) Field of Classification Search ........... None
See application file for complete search history.

(56) References Cited

U.S. PATENT DOCUMENTS

| 5,424,186 A * | 6/1995 | Fodor et al. .......... 435/6 |
| 5,429,807 A | 7/1995 | Matson et al. |
| 5,550,063 A | 8/1996 | Bogart |
| 5,552,272 A | 9/1996 | Bogart |
| 5,629,214 A | 5/1997 | Crosby |
| 5,631,734 A | 5/1997 | Stern et al. |
| 5,658,802 A | 8/1997 | Hayes et al. |
| 5,812,272 A | 9/1998 | King et al. |
| 5,847,105 A | 12/1998 | Baldeschwieler et al. |
| 6,008,892 A | 12/1999 | Kain et al. |
| 6,048,695 A * | 4/2000 | Bradley et al. .......... 435/6 |
| 6,060,237 A | 5/2000 | Nygren et al. |
| 6,177,990 B1 | 1/2001 | Kain et al. |
| 6,258,454 B1 | 7/2001 | Lefkowitz et al. |
| 6,444,268 B1 | 9/2002 | Lefkowitz et al. |
| 2002/0028445 A1 | 3/2002 | Laibinis et al. |
| 2002/0132261 A1 | 9/2002 | Dorsel et al. |

FOREIGN PATENT DOCUMENTS

| WO | WO 96/35971 | 11/1996 |
| WO | WO 99/54736 | 10/1999 |
| WO | WO 01/66244 | 9/2001 |

* cited by examiner

*Primary Examiner*—Jeanine A. Goldberg

(57) ABSTRACT

A method of producing a front surface modified substrate, which substrate includes a metal layer, and which is useful in the fabrication of an array of multiple probes bonded to a front surface of a substrate at different features of the array. The method includes providing the substrate wherein the front surface displays functional groups. The front surface is contacted with linker molecules each having a group which binds the linker molecule to the front surface following a reaction with a surface displayed functional group, which reaction does not produce a reagent which attacks the metal layer. To fabricate an array the front surface may be contacted with the probes or probe precursors to bind the probes or probe precursors to the front surface bound linker molecules.

22 Claims, 4 Drawing Sheets

Scheme 1 FIG. 4

Scheme 2 FIG. 5

LINKING TO CHEMICAL ARRAY ASSEMBLIES WITH METAL LAYERS

FIELD OF THE INVENTION

This invention relates to arrays, such as polynucleotide arrays (for example, DNA arrays), which are useful in diagnostic, screening, gene expression analysis, and other applications.

BACKGROUND OF THE INVENTION

In the following discussion and throughout the present application, while various references are cited no cited reference is admitted to be prior art to the present application.

Chemical arrays, such as polynucleotide or protein arrays (for example, DNA or RNA arrays), are known and are used, for example, as diagnostic or screening tools. Polynucleotide arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon reading the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated by depositing previously obtained biopolymers (such as from synthesis or natural sources) onto a substrate, or by in situ synthesis methods. Methods of depositing obtained biopolymers include loading then touching a pin or capillary to a surface, such as described in U.S. Pat. No. 5,807,522 or deposition by firing from a pulse jet such as an inkjet head, such as described in PCT publications WO 95/25116 and WO 98/41531, and elsewhere. Such a deposition method can be regarded as forming each feature by one cycle of attachment (that is, there is only one cycle at each feature during which the previously obtained biopolymer is attached to the substrate). For in situ fabrication methods, multiple different reagent droplets are deposited by pulse jet or other means at a given target location in order to form the final feature (hence a probe of the feature is synthesized on the array substrate). The in situ fabrication methods include those described in U.S. Pat. No. 5,449,754 for synthesizing peptide arrays, and in U.S. Pat. No. 6,180,351 and WO 98/41531 and the references cited therein for polynucleotides, and may also use pulse jets for depositing reagents. The in situ method for fabricating a polynucleotide array typically follows, at each of the multiple different addresses at which features are to be formed, the same conventional iterative sequence used in forming polynucleotides from nucleoside reagents on a support by means of known chemistry. This iterative sequence can be considered as multiple ones of the following attachment cycle at each feature to be formed: (a) coupling an activated selected nucleoside (a monomeric unit) through a phosphite linkage to a functionalized support in the first iteration, or a nucleoside bound to the substrate (i.e. the nucleoside-modified substrate) in subsequent iterations; (b) optionally, blocking unreacted hydroxyl groups on the substrate bound nucleoside (sometimes referenced as "capping"); (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The coupling can be performed by depositing drops of an activator and phosphoramidite at the specific desired feature locations for the array. A final deprotection step is provided in which nitrogenous bases and phosphate group are simultaneously deprotected by treatment with ammonium hydroxide and/or methylamine under known conditions. Capping, oxidation and deprotection can be accomplished by treating the entire substrate ("flooding") with a layer of the appropriate reagent. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in another flooding procedure in a known manner. Conventionally, a single pulse jet or other dispenser is assigned to deposit a single monomeric unit.

The foregoing chemistry of the synthesis of polynucleotides is described in detail, for example, in Caruthers, *Science* 230: 281–285, 1985; Itakura et al., *Ann. Rev. Biochem.* 53: 323–356; Hunkapillar et al., *Nature* 310: 105–110, 1984; and in "Synthesis of Oligonucleotide Derivatives in Design and Targeted Reaction of Oligonucleotide Derivatives", CRC Press, Boca Raton, Fla., pages 100 et seq., U.S. Pat. Nos. 4,458,066, 4,500,707, 5,153,319, 5,869,643, EP 0294196, and elsewhere. The phosphoramidite and phosphite triester approaches are most broadly used, but other approaches include the phosphodiester approach, the phosphotriester approach and the H-phosphonate approach. The substrates are typically functionalized to bond to the first deposited monomer. Suitable techniques for functionalizing substrates with such linking moieties are described, for example, in Southern, E. M., Maskos, U. and Elder, J. K., Genomics, 13, 1007–1017, 1992. In the case of array fabrication, different monomers and activator may be deposited at different addresses on the substrate during any one cycle so that the different features of the completed array will have different desired biopolymer sequences. One or more intermediate further steps may be required in each cycle, such as the conventional oxidation, capping and washing steps in the case of in situ fabrication of polynucleotide arrays (again, these steps may be performed in flooding procedure).

Further details of fabricating biopolymer arrays by depositing either previously obtained biopolymers or by the in situ method are disclosed in U.S. Pat. Nos. 6,242,266, 6,232,072, 6,180,351, and 6,171,797. In fabricating arrays by depositing previously obtained biopolymers or by the in situ method, typically each region on the substrate surface on which an array will be or has been formed ("array regions") is completely exposed to one or more reagents. For example, in either method the array regions will often be exposed to one or more linker compositions to form a suitable linker layer on the surface which binds to both the substrate and biopolymer or biomonomer. In in situ fabrication the array regions will also typically be exposed to the oxidizing, deblocking, and optional capping reagents. Similarly, particularly in fabrication by depositing previously obtained biopolymers, it may be desirable to expose the array regions to a suitable blocking reagent to block locations on the surface at which there are no features from non-specifically binding to target. Particularly useful linker compositions and methods are disclosed in U.S. Pat. Nos. 6,319,674 and 6,444,268. Such methods may use trichlorosilane functional groups to link the silane to the substrate.

In array fabrication, the quantities of polynucleotide available are usually very small and expensive. Additionally, sample quantities available for testing are usually also very small and it is therefore desirable to simultaneously test the same sample against a large number of different probes on an array. These conditions require use of arrays with large numbers of very small, closely spaced features. When the array is read, such as by detecting light emitted from features in response to an interrogating light, the total detected light signal from a feature may therefore be very low. It is important then that the detected light intensity not be affected by factors other than the composition of the features (including any sample bound to them). Such extraneous factors can lead to a decrease in detected signal from features of the array, as well as variations in detected signal across the array and from array to array which are unrelated to the feature compositions. The resulting decreased or varied detected signal can lead to a misinterpretation of a result from the array.

It would be desirable then to provide an array substrate, and a method for producing such a substrate, which does not introduce a substantial decrease or extraneous variations into the detected signals during array reading.

SUMMARY OF THE INVENTION

The present invention recognizes that substrates for array fabrication which contain a metal layer, can be sensitive to chemical conditions such as those used during a reaction to bind linker molecules onto the substrate surface. Any alterations in the metal layer due to undesired chemical reactions at the metal layer during attachment of linker molecules or other reactions, can lead to a diminished reflectivity or a non-uniform reflectivity within an array or between different arrays. This can adversely affect detected signals from array features and lead to a misinterpretation of results from an experiment or diagnostic test. For example, linking of a trichlorosilane with surface displayed hydroxyl groups under hydrolytic conditions may produce hydrochloric acid which may then etch a metal layer of the substrate.

The present invention then, provides in one aspect, a method of producing a substrate with a modified front surface, which substrate includes a metal layer. The method may include providing the substrate wherein the front surface displays functional groups (such as hydroxyl groups). The front surface may be contacted with linker molecules each having a group (such as a silyloxy group, for example a silyl alkoxide such as an ethoxide) which binds the linker molecule to the front surface following a reaction with a surface displayed functional group (for example, through an ether linkage following reaction of a silyloxyl group with a surface displayed hydroxy group). The reaction may be one which does not produce a reagent which attacks the metal layer (for example, one which does not produce an acid). The substrate may include a back layer, a front layer on which the front surface is located, and a metal layer positioned between the back layer and front layers. Either of the front or back layer may be transparent and can, for example, be a plastic or glass, or other material, while the metal layer can, for example be a light reflective layer comprising chromium.

The present invention further provides a method of fabricating an array of multiple probes, such as biopolymers, bonded to a front surface of a substrate at different features of the array, which substrate includes a metal layer. The method includes producing a substrate with a modified front surface according to a method of the present invention. The front surface may be contacted with the probes or probe precursors to bind the probes or probe precursors to the front surface bound linker molecules and produce the array. Various types of probes may be used, for example, polymers such as nucleic acids or poly-amino acids. For example, when the probes are polymers they may be produced on the front surface by in situ synthesis comprising repeatedly contacting each of multiple different feature locations with probe precursors. Alternatively, the complete probe (polymer or not) may be deposited onto the front surface. In either situation though, it may be necessary to first convert a linker functional group to a probe or probe precursor reactive functional groups where the probe or probe precursor deposited onto the front surface does not bind to the surface bound linker molecules following contact.

The various aspects of the present invention can provide any one or more of the following and/or other useful benefits. For example, adverse affects on the metal layer from the chemistry used to bind linkers to the front surface, may be reduced or avoided, thereby producing a substrate with good light reflectivity and reflectivity uniformity from the front side.

BRIEF DESCRIPTION OF THE DRAWINGS

To facilitate understanding, the same reference numerals have been used, where practical, to designate the same elements that are common to the figures. Drawings are not necessarily to scale.

DETAILED DESCRIPTION OF EMBODIMENTS OF THE INVENTION

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

An "array", unless a contrary intention appears, includes any one, two or three-dimensional arrangement of addressable regions bearing a particular chemical moiety or moieties (for example, biopolymers such as polynucleotide sequences) associated with that region. Each region may extend into a third dimension in the case where the substrate is porous while not having any substantial third dimension measurement (thickness) in the case where the substrate is non-porous. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). An array feature is generally homogenous and the features typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" or "array characteristics", refers to one or more physical, chemical or biological characteristics of the array, such as feature positioning, one or more feature dimensions, or some indication of an identity or function (for example, chemical or biological) of a moiety at a given location, or how the array should be handled (for example, conditions under which the array is exposed to a sample, or array reading specifications or controls following sample exposure). "Hybridizing" and "binding", with respect to polynucleotides, are used interchangeably.

A "plastic" is any synthetic organic polymer of high molecular weight (for example at least 1,000 grams/mole, or even at least 10,000 or 100,000 grams/mole.

"Flexible" with reference to a substrate or substrate web, references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C.

A "web" references a long continuous piece of substrate material having a length greater than a width. For example, the web length to width ratio may be at least 5/1, 10/1, 50/1, 100/1, 200/1, or 500/1, or even at least 1000/1.

"Reference unit" in relation to fluorescence measurements herein means the maximum fluorescence obtainable from a fused silica, or one-third the maximum value obtainable from a borosilicate glass. The fluorescence measurements for reference units herein, unless otherwise indicated, are integrated fluorescence emission energies from 547 nm to 597 nm, which result from a 1 mm thick section of material, using a monochromated high pressure Xe lamp excitation source centered at 532 nm with a width at half-maximum of about 5 nm. All ratios assume the same unit area of illuminated material. The following may be used as the foregoing referenced materials (available from the National Institute of Standards and Technology, Maryland, U.S.A.): fused silica—Standard Sample 198; borosilicate glass—Standard Reference Material 93a.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. An array "assembly" may be the array plus only a substrate on which the array is deposited, although the assembly may be in the form of a package which includes other features (such as a housing with a chamber). A "chamber" references an enclosed volume (although a chamber may be accessible through one or more ports). It will also be appreciated that throughout the present application, that words such as "front", "back","top", "upper", and "lower" are used in a relative sense only. "Fluid" is used herein to reference a liquid. Reference to a singular item, includes the possibility that there are plural of the same items present. "May" refers to optionally. Any recited method can be carried out in the ordered sequence of events as recited, or any other logically possible sequence.

A "linking layer" bound to the surface may be less than 200 angstroms or even less than 10 angstroms in thickness (or less than 8, 6, or 4 angstroms thick). Such layer may have a polynucleotide, protein, nucleoside or amino acid minimum binding affinity of $10^4$ to $10^6$ units/$\mu^2$. Layer thickness in the present invention can be evaluated using UV or X-ray elipsometry.

A "group" in relation to a chemical formula, includes both substituted and unsubstituted forms of the group. Any substituents should be selected so as to not interfere with the desired reaction.

"Lower alkyl group" is an alkyl group with from 1 to 6 C atoms, and may only have any one of 1, 2, 3, or 4 C atoms.

By a metal layer not being "attacked" or a reagent which does "not attack" a metal layer, or similar terms, is meant that after exposure of the substrate to a reagent ceases in a method, the metal layer is not degraded in overall light power reflectivity on the substrate (measured at 532 nm or 633 nm), by not more than 30% (for example, not more than 10% or even not more than 5% or 2%), or that such overall light power reflectivity has not decreased in uniformity by more than a predetermined amount. The uniformity requirement can be measured by using laser light centered at 532 nm or 633 nm (with a ½ height width of about 5 nm) and measuring reflected light with a detected pixel size of 5 µm by 5 µm. If the measured reflected light intensity for 80% of the detected pixels before and after exposure to the reagent does vary by less than 5% (for example, less than 2% or 1%) then this can be classified as no decrease in uniformity. One way of indirectly measuring any change in reflectivity is to illuminate a substrate (such as with laser light of either of the wavelengths previously referenced) from a forward direction and measure from the forward direction any change in measured fluorescence (for example, at 547 nm or 597 nm) from a back layer located behind the reflective layer. This will work well when the back layer is strongly fluorescent (for example, when the back layer is a polyetheretherketone). If the metal layer has not been attacked by the exposure to the reagent, then any increase in fluorescence should not interfere with the measured fluorescent signal from a final array on the substrate. Particularly, any increase in fluorescence either overall or from 80% of pixels of the previously referenced size, should be less than 2% (for example, less than 1%) and ideally zero, relative to the original substrate before the exposure to the reagent. Such fluorescence can be measured, for example, on a scanner such as the AGILENT ARRAY SCANNER manufactured by Agilent Technologies, Palo Alto, Calif. Other fluorimeters may also be used.'

The steps of any method herein may be performed in the recited order, or in any other order that is logically possible. All patents and other references cited in this application, are incorporated into this application by reference except insofar as where any definitions in those references conflict with those of the present application (in which case the definitions of the present application are to prevail).

Figure 1:
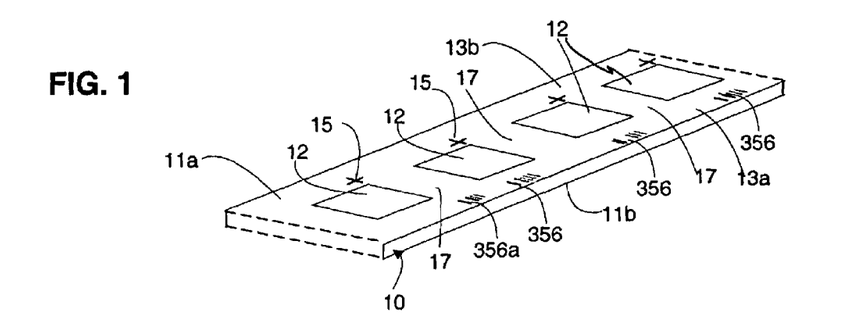
FIG. 1 illustrates an array assembly in the form of a web carrying multiple arrays, such as may be fabricated by methods of the present invention.
Figure 2:
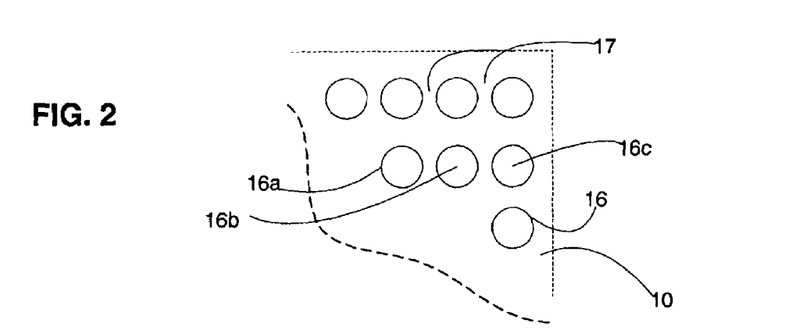
FIG. 2 is an enlarged view of a portion of FIG. 1 showing multiple ideal spots or features.
Figure 3:
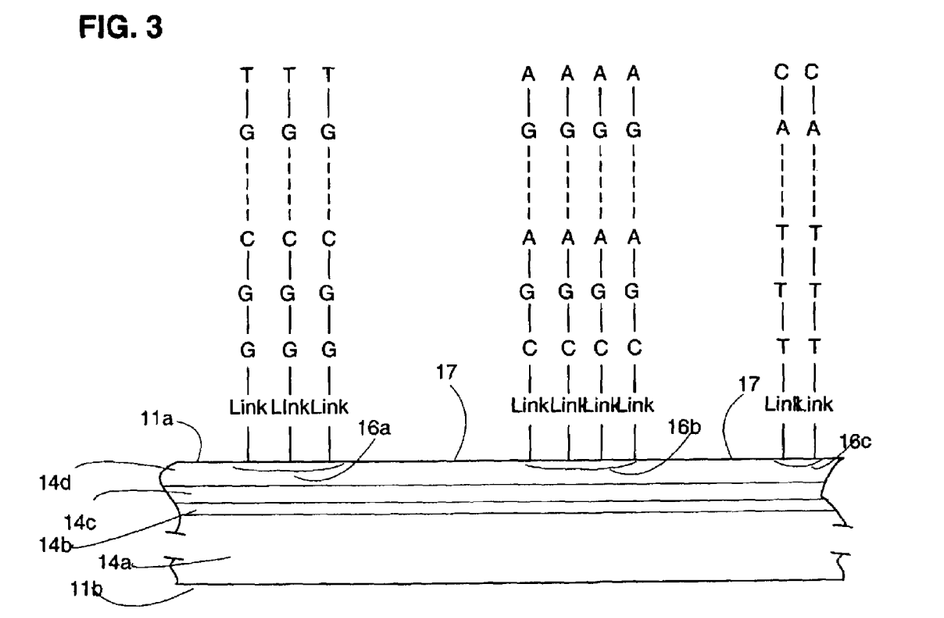
FIG. 3 is an enlarged illustration of a portion of FIG. 2.

Referring first to FIGS. 1–3, methods of the present invention may generate an array assembly which includes a substrate which can be, for example, in the form of an elongated flexible web (or ribbon) 10 carrying one or more arrays 12 disposed along a front surface 11a of web 10 and separated by inter-array areas 17. A back side 11b of web 10 does not carry any arrays 12. The arrays on web 10 can be designed for testing against any type of sample, whether: a trial sample; reference sample;, a combination of the foregoing; or a known mixture of polynucleotides, proteins, polysaccharides and the like (in which case the arrays may be composed of features carrying unknown sequences to be evaluated). While only four arrays 12 are shown in FIG. 1, it will be understood that web 10 and the embodiments to be used with it, may use any number of desired arrays 12 such as at least five, ten, twenty, fifty, or one hundred (or even at least five hundred, one thousand, or at least three thousand). The foregoing numbers of arrays will typically be arranged end to end along the lengthwise direction of web 10. To accommodate arrays 12, web 10 may be at least 100 cm (or at least 200 or 500 cm) in length, or may even be greater than 1 m (or greater than 2, 5 or 10 or 100 m) in length, with a width, for example, of less than 100 cm, or even less than 50, 30, 10, 5 or 1 cm. While only one array is positioned across the width of web 10, it is possible there could be more (for example two or three). Typically then, the ratio of the number of arrays 12 positioned lengthwise along web 10 to the number across the width may be at least 10/1, 20/1, 50/1, 100/1, or even at least 500/1 or at least 1000/1. Depending upon intended use, any or all of arrays 12 may be the same or different from one another and each will contain multiple spots or features 16 of biopolymers in the form of polynucleotides. A typical array may contain from more than ten, more than one hundred, more than one thousand or ten thousand features, or even more than from one hundred thousand features. All of the features 16 may be different, or some or all could be the same. In the case where arrays 12 are formed by the conventional in situ or deposition of previously obtained moieties, as described above, by depositing for each feature a droplet of reagent in each cycle such as by using a pulse jet such as an inkjet type head, interfeature areas 17 will typically (but not essentially) be present which do not carry any polynucleotide. It will be appreciated though, that the interfeature areas 17 could be of various sizes and configurations. It will also be appreciated that there need not be any space separating arrays 12 from one another. Each feature carries a predetermined polynucleotide (which includes the possibility of mixtures of polynucleotides). As per usual, A, C, G, T represent the usual nucleotides. L (see FIG. 3 in particular) represents a linker molecule covalently bound to the front surface and a first nucleotide.

Web 10 also has opposite edge margins 13a, 13b along front surface 11a, along one edge margin 13a of which are provided identifiers in the form of bar codes 356. Identifiers such as other optical or magnetic identifiers could be used instead of bar codes 356 which will carry the information discussed below. Each identifier is positioned adjacent an associated array 12. However, this need not be the case and identifiers such as bar code 356a can be positioned elsewhere. Further, a single identifier might be provided which is associated with more than one array 12 and such one or more identifiers may be positioned on a leading or trailing end (neither shown) of web 10. Alignment fiducial marks 15 may also be present along edge margin 13b, each fiducial 15 associated with a corresponding adjacent array 12, for the purposes discussed below. Alternatively, bar codes 356 can be positioned along one or both of the edge margins 13a, 13b on back surface 11b. This can be advantageous since, as discussed below, back surface 11b may be of a plastic base layer onto which markings might be more easily provided (by printing or laser ablation) than onto front surface 11a. Web 10 may, for example, be at least 100 cm in length, or even at least 0.5 m or at least 1, 2, 5 or 10 m in length, with a width of at least 3 mm or even at least 5 mm, or 1, 2, 5 or 10 cm.

FIGS. 2 and 3 illustrate ideal features 16 of an array 12 where the actual features formed are the same as the target (or "aim") features, with each feature 16 being uniform in shape, size and composition, and the features being regularly spaced. Such an array when fabricated by drop deposition methods, would require all reagent droplets for each feature to be uniform in shape and accurately deposited at the target feature location. In practice, such an ideal result is difficult to obtain due to fixed and random errors during fabrication.

It will be seen from FIG. 3 that web 10 may have a number of different layers. A back layer 14a forms the greatest thickness and may consist of a flexible material such as a plastic, for example as a polyolefin film (such as polypropylene, polyethylene, polymethylpentene) or polyetheretherketone, polyimide, any of the flurocarbon polymers or other suitable flexible thermoplastic polymer film. The material of base layer 14a is best selected to provide stable dimensional, mechanical, and chemical properties under the conditions web 10 will be used. For example, for a polynucleotide arrays web 10 will be subject to elevated temperatures (for example, 60°) for long times (for example, 12 hours) in aqueous environments. Polyester or aramid films exposed to such conditions may tend to swell or degrade. When the type of arrays 12 and the conditions to which the layer 14a will be exposed, are selected, back layer 14a can be selected for dimensional, mechanical and chemical stability under such conditions by reference to many known polymer film characteristic sources such as: "New Characterization Techniques for Thin Polymer Films", Ho-Ming Tong (Editor), Luu T. Nguyen (Editor), ISBN: 0-471-62346-6; "Polymer Surfaces and Interfaces II", W. J. Feast (Editor), H. S. Munro (Editor), R. W. Richards (Editor), ISBN: 0-471-93456-9; "Functional Organic and Polymeric Materials: Molecular Functionality—Macroscopic Reality", Tim H. Richardson (Editor), ISBN: 0-471-98724-7; the polymer property searchable database "Polymers—A Property Database", Ellis, Bryan Sheffield University, UK, ISBN/ISSN: 0849310555; "Handbook of Plastic Materials and Technology", (Irvin, I Rubin, ed); "Modern Plastics Encyclopedia"; "Plastics Design Library Chemical Resistance"; the guide available on the world wide web page boedeker.com/mguide.htm which is Boedeker Material Selection Guide for plastics; or the world wide web site at Knovel.com which also offers an on-line polymers properties database. Back layer 14a will typically have a thickness of more than 1 µm (or more than 5 µm) and less than 500 µm (or even less than 100, 50, 25, or 15 µm). However, back layer 14a can be of a rigid material, such as silica or glass when flexibility is not required.

Web 10 also includes a transparent front layer 14d which may be a glass or silica layer 14d, as well as a reflective metal layer 14c between the back and front layers 14a, 14d. Reflective layer 14c may be chromium or other suitable metal film deposited by vacuum deposition, plasma enhanced chemical vapor deposition or other means, onto back layer 14c or onto an optional intermediate bonding layer 14b. Bonding layer 14b, if used, may be any suitable material which is flexible at the thickness used and bonds to both back layer 14a and metal layer 14c. Reflectively coated plastic films are well known and commercially available. Front layer 14d may be deposited onto reflective layer 14c by sputtering, plasma enhanced chemical vapor deposition or similar techniques. Several manufacturers have commercial capabilities for providing films coated with metal and glass layers, for example, Sheldahl Corporation, Northfield, Minn. (see their world wide web site at sheldahl.com), and General Atomic, San Diego, Calif. (having a world wide web site at ga.com) Front layer 14d may have any suitable thickness, for example greater than 1, 10 or 100 nm, and less than 1000, 700, or 400 nm but typically has a thickness about ¼ wavelength of the light used to illuminate array features during reading, or an odd multiple of that amount. For example, 40 to 200 nm, or 60 to 120 nm (or even 80 to 100 nm), or an odd integer multiple of any of the foregoing thickness ranges (for example, 300 nm may be used) provided the layer is not so thick that web 10 is no longer flexible in those situations where flexibility is desired. Selecting front layer 14d of an appropriate thickness (such as approximately ¼ the wavelength of the interrogating light) as described in U.S. patent application Ser. No. 10/080641 titled "Multi-Featured Arrays With Reflective Coating" by Dorsel et al., can be advantageous in enhancing the interrogating light power at the front surface and the detected signal as a result of constructive interference, as described in that application and U.S. Pat. No. 6,008,892.

Metal layer 14c, and bonding layer 14b may each have a thickness of less than 1000 nm, 500 nm, 200 nm, 50 nm, or even less than 20, 10, 5 or 1 nm (but in any case, for example, more than 0.1 or 0.5 nm). In one example, bonding layer 14b may be 10 nm. Metal layer 14c may particularly be chosen to have a thickness such that it is opaque to the wavelength of the light used for illuminating the features during array reading. Front layer 14d may particularly have a thickness and transparency selected as described in U.S. patent application Ser. No. 10/080641 titled "Multi-Featured Arrays With Reflective Coating" by Andreas Dorsel et al, while metal layer 14c may meet the reflectivity requirements in relation to the illuminating light as mentioned in that application. For example, metal layer 14c may reflect at least 10% of the incident light, or at least 20%, 50%, 80% or at least 90%, or even at lest 95%, of the incident light (for example, illuminating light of 532 nm or 633 nm). As mentioned previously, this and the other references cited herein are incorporated into this application by reference. However, the front layer 14d and reflective layer 14c need not necessarily meet those requirements.

In the above configuration of web 10, the use of a front layer 14d allows the use of chemistries (such as attaching linker molecules) which may not be possible absent that layer (for example, attaching linker molecules to reflective layer 14c). Furthermore, using metal layer 14c not only can provide the useful characteristics mentioned in the above referenced patent application Ser. No. 09/493,958, but can avoid undesirable optical characteristics of the plastic back layer 14a (for example, undesirable fluorescence, and in the case of a plastic web that absorbs the incident light energy, excessive heating and possible melting of the substrate). This allows for the ability to use back layers 14a of a material which may have a high fluorescence and/or high absorbance of incident light. For example, the back layer 14a may have a fluorescence of at least five or ten (or even at least: twenty, fifty, one-hundred, or two-hundred) reference units, and/or an absorbance of the illuminating light used to read arrays 12 (for example, light of 532 nm or 633 nm) of at least 5%, 10%, 20%, or 50% (or even at least 70%, 90% or 95%).

Figure 4:
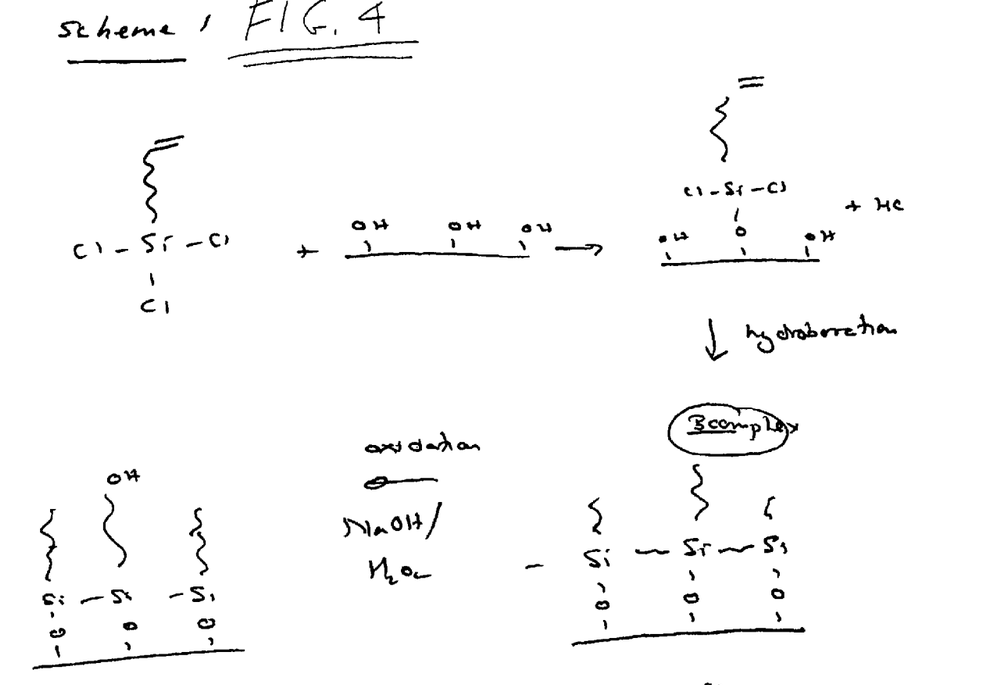
FIG. 4 illustrates a method of binding linker molecules to a front surface of a substrate having a metal layer, using trichlorosilane.

Turning now to FIG. 4, a known method for attaching linker molecules to a substrate is shown. In this method linker molecules having both an unsaturated group and a trichlorosilane functional group, are exposed to a surface displaying hydroxyl groups (which may be hydroxyl groups on the surface of glass or silica). Following linking, hydroboration of the unsaturated group followed by oxidation in basic peroxide solution results in terminal hydroxyl groups which will subsequently react upon contact with, and covalently bind to, activated phosphoramidites deposited onto the front surface during array fabrication. However, the first step in the method of FIG. 4 (bonding of the linker molecules) results in the production of hydrochloric acid. This now appears to attack metal layer 14c producing a layer of irregular reflectivity, despite the presence of front layer 14d.

Figure 5:
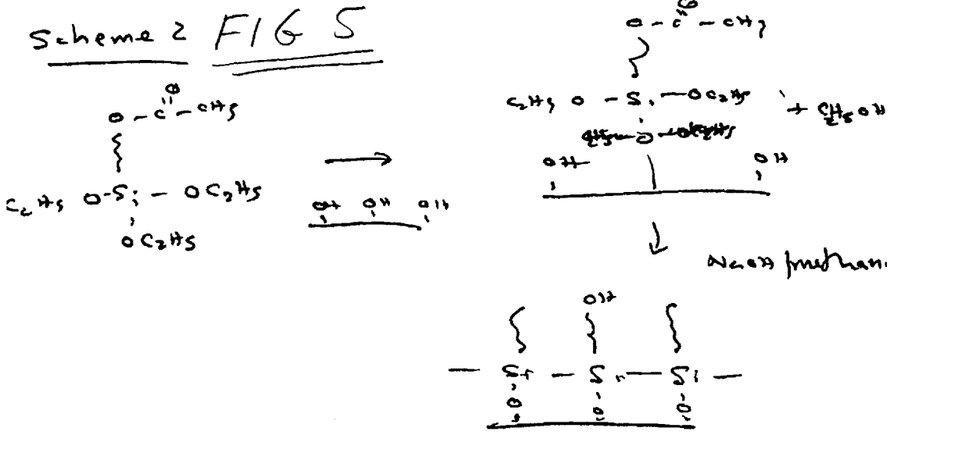
FIG. 5 illustrates a method of binding linker molecules to a front surface of a substrate having a metal layer, according to the present invention.

On the other hand, FIG. 5 illustrates a method used in the present invention for producing a modified front surface of a substrate 10 as illustrated in FIG. 3, which has a metal layer 14c. In FIG. 5 linker molecules having a triethoxy silane functional group, are brought into contact with the substrate front surface 11a. At least one of the ethoxy groups of each linker molecule reacts with a surface displayed hydroxyl group of layer 14d (such as a hydroxyl group present on a layer 14d of glass or silicon dioxide) to covalently bind the linker molecule to front surface 11a through an ether linkage following the reaction. Note that unlike the method of FIG. 4, no reagent is produced (specifically, no acid) which will attack the substrate metal layer. Next the free acetate group can be hydrolyzed under alkaline conditions to free hydroxyl groups using, for example, NaOH in methanol such as described in U.S. patent application Ser. No. 10/106685 titled "Methods For Generating Ligand Arrays" filed Mar. 25, 2002.

The effect of an acid produced by a method of FIG. 4 in attacking the metal layer, despite the presence of front layer 14d, can be shown by comparison of the results from the following two examples.

In the following Example 1 a front surface of a substrate consisting of a back layer of polyetheretherketone, a front layer of 100 nm thick silica (SiO$_2$), and an intermediate reflective chromium layer 200 nm in thickness, is provided with bound linker molecules according to the following procedure:

a) 4 mls (range 2 to 6 mls) of a solution of 98% decyltriethoxysilane and 2% 11-triethoxysilylundecyl acetate are stirred overnight in 100 mls of toluene. About 400 micrograms of water per ml (range 300 to 450 ug/ml) had previously been dissolved in the toluene.

b) The front surface of the substrate is then treated to the solution from (a) for 2 hours at room temperature after which time they were cleaned in a wash of firstly toluene, secondly methanol and finally water.

c) To bind deposited phosphoramidite probe precursors to the linker molecules on the front surface upon contact, the acetate functional groups are to be converted to reactive functional groups using the following procedure. Namely, the acetate group was then hydrolyzed with 0.2N sodium methoxide (or any alkoxide) in alcoholic solution for 5 mins at room temperature. This produces a monolayer terminated with a hydroxyl group. Alternative methods of hydrolysis include treating the acetate group with (A) an aqueous solution of an alkali, for instance sodium or potassium hydroxide, or (B) an aqueous solution of an acid at 50 degrees C. for one hour. However, care must be taken because aqueous solutions, but not alcohol solutions, tend to hydrolyze the siloxyl linkage quite easily, that is, they tend to cleave the —O—Si— bond. In addition, dilute acid solutions will attack the flexible substrate and can only be prevented from doing so if the integrity of the protective silane monolayer is perfect. Hence the first is better to use the alcoholic solution.

Figure 6:
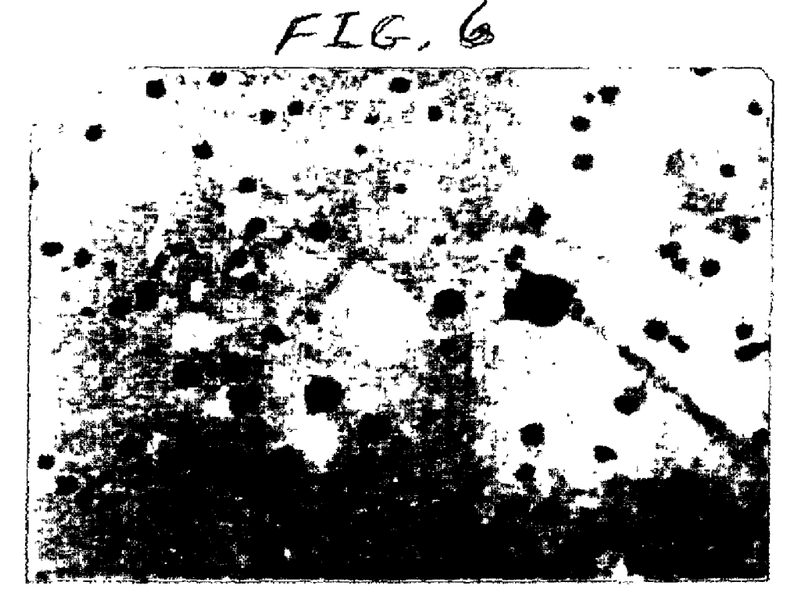
FIGS. 6 and 7 are photographs of a front surface of a substrate having a metal layer to which linker molecules were bound using a method according to FIG. 4.
Figure 7:
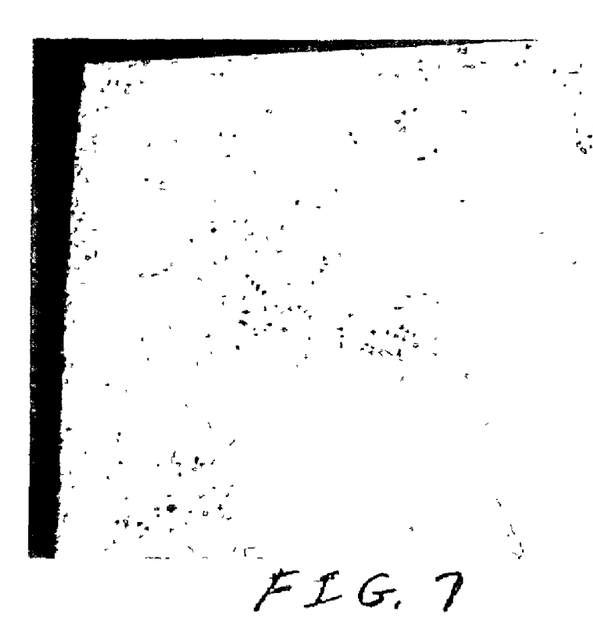

A first nucleoside phosphoramidite was deposited onto the substrate to bind to the linker molecules through reaction with their terminal hydroxyl groups. The front surface of the resulting substrate was then photographed at 40× (FIG. 6) and 10× (FIG. 7). Note that the substrate is relatively uniform in its reflection of light indicating that there are few defects in the metal layer as a result of reagent attack upon it.

Figure 8:
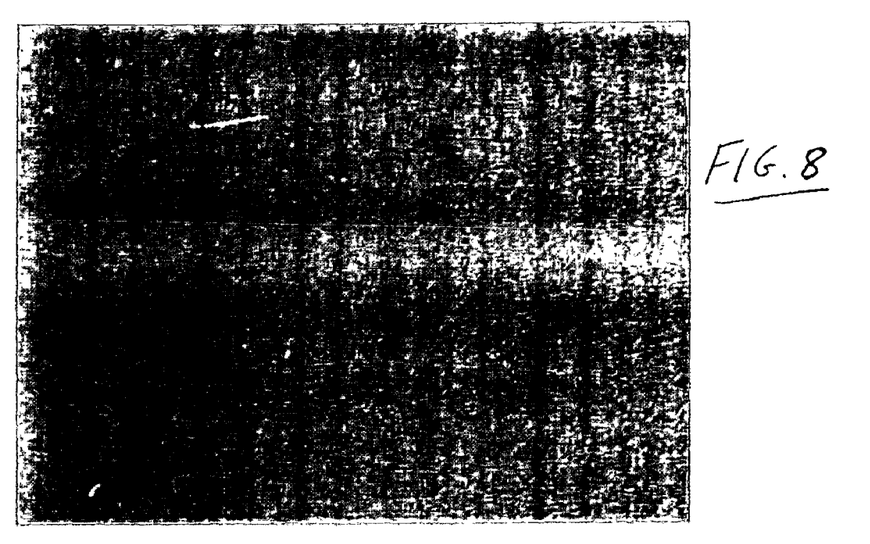
FIGS. 8 and 9 are photographs of a front surface of a substrate having a metal layer to which linker molecules were bound using a method of the present invention according to FIG. 5.
Figure 9:
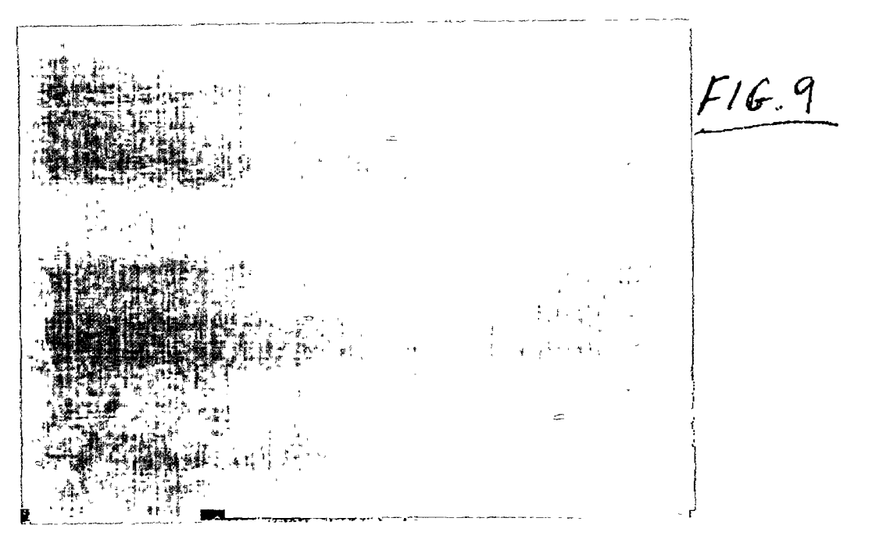

In comparison, the effect of an acid resulting from using a method show in FIG. 4 is illustrated in the following Example 2. In this Example, the procedure of Example 1, parts (a) and (b) was repeated except the decyltriethoxysilane was replaced with decyltrichlorosilane, and the 11-triethoxysilylundecyl acetate was replaced with undecenyltrichlorosilane (as disclosed in U.S. Pat. No. 6,444,268). The resulting surface was then photographed as in Example 1 at 40× (FIG. 8) and 10× (FIG. 9). No phosphoramidite was exposed to the surface in this Example 2 since the surface resulting from steps (a) and (b) was very poor quality as seen in FIGS. 8 and 9.

It can be seen by comparing FIGS. 6 and 8, and FIGS. 7 and 9, that using a method of the present invention in which no reagent is produced which attacks the metal layer despite the presence of front layer 14d, produces substrates with more uniform light reflection across its front surface than when a method is used which does produce a metal layer attacking reagent.

In preparing a substrate surface by a method of the present invention, other groups can be used which bind the linker molecule to the front surface and which also do not produce an acid as a result of the reaction. For example, a linker can be used which in general has any silyloxy group which binds the linker molecule to the front surface through an ether linkage following reaction with a surface displayed hydroxyl group. By a "silyloxy" group is meant a group of the formula:

$$—Si—O— \quad (1)$$

where the Si may also be bonded to two H or may also be substituted with one or two other groups, and the O is not linked to an H. For example, a group of formula (1) may have a hydrocarbyloxy group linked to the Si, and may be of the formula:

$$(R^2)_m\text{-}(L)_n\text{-Si—}OR^p \quad (2)$$

in which: $R^p$ is a hydrocarbyl group such as an alkyl group (for example, a lower alkyl group); L represents a linker component and n is 0 or 1, such that a linker may or may not be present; and $R^2$ represents a reactive functional group which will bind a deposited probe or probe precursor (such as a nucleoside phosphoramidite) upon contact, or a linker functional group which can be converted to such a reactive functional group. If L is present, it will generally be a $C_1$–$C_{24}$ hydrocarbylene linking group, for example a $C_{10}$–$C_{18}$ alkylene. There may be one, two, or three $R^p$ groups present on the Si in formula (2), and when there is more than one any of them may be the same or different from one another. For example formula (2) could include a trialkoxy group of the formula —Si(OR$_p$)$_3$ where any of the R$_p$ may be the same or different alkyl group (for example each $R^p$ could be a lower alkyl group, such as an ethyl group so that the foregoing group is the triethoxy).

As already mentioned, the Si in formula (2) may be bonded to two H, either of which may be replaced by a substituent (such as a lower alkyl or alkoxy). $R^2$ in formula (2) should be selected so as to not unduly interfere with the binding of the linker molecules to the substrate front surface. For example, $R^2$ may be a carboxylic ester functional group such that upon coupling, a linker molecule of formula (2) provides the surface with bound linking groups of the formula:

$$—Si\text{-}(L)_n\text{-}R^2 \quad (3)$$

where $R^2$ is a hydrolyzable carboxylic ester group. Of course, if the $R^x$ and $R^y$ are not leaving groups, the surface moieties provided will actually be —SiR$^x$R$^y$-(L)$_n$-R$^2$ groups, which applicants intend to encompass by the more generic representation —Si-(L)$_n$-R$^2$ in formula (3).

In formula (2) $R^2$ may be a convenient hydrolyzable functional group that produces a hydroxyl function group (—OH) upon exposure to either acid or alkali hydrolysis conditions, that is, $R^2$ is any convenient acid or alkali hydrolyzable group. In many embodiments, the acid or alkali hydrolyzable functional group is a group that yields a free carboxylic acid upon hydrolysis. In many of these embodiments, the hydrolyzable functional group is an ester. As such, in many embodiments, the $-Si-(L)_n-R^2$ surface groups are esters of a carboxylic acid and a long chain alcohol (so that they include a carboxylic ester functional group), where the long chain alcohol is L and is covalently bound to the substrate surface via the Si linkage. Viewed another way, the $-Si-(L)_n-R^2$ surface groups may be long chain esters that are hydrolyzable to yield a long chain alcohol that is bound to the substrate surface and free carboxylic acid, i.e., a surface bound hydroxyl group and a free carboxylic acid.

In many of the above embodiments, $R^2$ may have the following formula: $O-(CO)-R^3$, where $R^3$ is, in many embodiments, an alkyl group, such as a lower alkyl group as defined above. However, $R^3$ may be any group that does not unacceptably interfere with the acid hydrolysis of the functional group to produce a hydroxyl group, as described in greater detail below. Specific groups of interest include, but are not limited to: acetyl, alkyl, alkenyl, amino, benzyl, hydroxyl, halo, and the like. If $R^2$ has the formula $O-(CO)-R^3$ then $(L)_n$ will be terminated by a hydroxyl group after either/acid or alkaline hydrolysis.

Other functional groups can be used for $R^2$ though. However, $R^2$ should be selected so as not to unduly interfere with the reaction of the linker molecules of with the substrate front surface. For example, if the linker molecules are to bind to surface displayed hydroxyl groups, then it will be best to avoid having hydroxyl groups present on the linker molecules during such surface binding. Other functional groups for $R^2$ then, include an alkylene group which can be converted to a hydroxyl group after the linker molecules are bound to the surface, using a method such as described in U.S. Pat. No. 6,258,454 incorporated herein by reference. When m is 0 in formula (2) there is no reactive functional group present to bind a probe or probe precursor, in which case L or the Si (when L is not present) terminate only with a relatively unreactive moiety such as H or an alkyl group (for example, a lower alkyl). Such a compound can be used in a method of the present invention when it is desired to control the density of probe or probe precursor binding reactive functional groups. In particular, the density of the $R^2$ hydrolyzable functional groups on the substrate surface, following reaction with the derivatizing composition, may be controlled by exposing the substrate front surface to a composition containing a mixture of compounds of formula (2), one of which has no reactive functional group $R^2$ present. That is, a higher proportion of a compound of formula (2) with $R^2$ present (a "second silane") will provide a greater density of $R^2$ groups, while a higher proportion of a compound of formula (2) without an R2 group (a "first silane") will give rise to a lower density of $R^2$ groups. Optimally, the first silane is present in the range of approximately 0 wt. % to 99.5 wt. % of the derivatization composition, for example in the range of approximately 90 wt. % to 99 wt. % of the composition, while the second silane correspondingly is present in the range of approximately 0.5 wt. % to 100 wt. % of the derivatization composition, for example in the range of approximately 1% wt. % to 10 wt. % of the composition.

In many embodiments, the resultant surface of the functionalized substrates contain both $-Si-R^1$ and $Si-(L)_n-R^2$ groups, present at a predetermined ratio, with the ratio determining both surface energy and density of functional groups. In other words, the functional surface of the substrate displays acid or alkali hydrolyzable functional groups. U.S. Pat. No. 6,258,454 provides a further description of the general process of derivatizing a surface with a composition containing a mixture of silanes. The procedures therein can be used in the present invention with the exception that groups which produce an acid upon linking to the surface (such as the trichlorosilane group) are replaced with non-acid producing functional groups (such as the silyloxy groups discussed above). Alkoxysilanes of formula (2) can be commercially purchased or obtained by well-known processes such as described in U.S. Pat. Nos. 4,491,669 and 6,150,550.

A substrate made by a method of the present invention, can be used in fabricating an array according to a method of the present invention. In this case, the substrate is contacted with the probes (for example, nucleic acids or proteins) to be deposited on the array or with probe precursors (such as nucleoside phosphoramidites). The deposited probes or probe precursors covalently bind to a reactive functional group on the linker molecules which are bound to the surface, upon contact with them. The deposition of drops containing probes or probe precursors to fabricate arrays in this manner is described in some detail in, for example, U.S. Pat. Nos. 6,242,266, 6,232,072, 6,180,351, 6,171,797,6,323, 403, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. Nos. 5,599,695, 5,753,788, and 6,329,143. Interfeature areas need not be present particularly when the arrays are made by photolithographic methods as described in those patents.

Following receipt by a user of an array made by a method of the present invention, it will typically be exposed to a sample (for example, to a fluorescently labeled polynucleotide or protein containing sample) and the array then read under known hybridizing conditions. Reading of the array may be accomplished by illuminating the array and reading the location and intensity of resulting fluorescence at multiple regions on each feature of the array. For example, a scanner may be used for this purpose which is similar to the AGILENT MICROARRAY SCANNER manufactured by Agilent Technologies, Palo Alto, Calif. Other suitable apparatus and methods are described in U.S. patent applications: Ser. No. 10/087447 "Reading Dry Chemical Arrays Through The Substrate" by Corson et al., and U.S. Pat. No. 6,406, 849. However, arrays may be read by any other method or apparatus than the foregoing and may include, for example, other optical techniques (for example, detecting chemiluminescent or electroluminescent labels). A result obtained from the reading followed by a method of the present invention may be used in that form or may be further processed to generate a result such as that obtained by forming conclusions based on the pattern read from the array (such as whether or not a particular target sequence may have been present in the sample, or whether or not a pattern indicates a particular condition of an organism from which the sample came). A result of the reading (whether further processed or not) may be forwarded (such as by communication) to a remote location if desired, and received there for further use (such as further processing).

Modifications in the particular embodiments described above are, of course, possible. For example, where a pattern of arrays is desired, any of a variety of geometries may be constructed other than the organized rows and columns of arrays 12 of FIG. 1. For example, arrays 12 can be arranged in a series of curvilinear rows across the substrate surface (for example, a series of concentric circles or semi-circles of spots), and the like. Similarly, the pattern of regions 16 may be varied from the organized rows and columns of features in FIG. 2 to include, for example, a series of curvilinear rows across the substrate surface (for example, a series of concentric circles or semi-circles of spots), and the like. Even irregular arrangements of the arrays or the regions within them can be used. However, the user should be provided with some means (for example, through the array identifier) of being able to ascertain at least some characteristics of the features (for example, any one or more of feature composition, location, size, performance characteristics in terms of significance in variations of binding patterns with different samples, or the like). The configuration of the array may be selected according to manufacturing, handling, and use considerations. The present methods and apparatus may be used to fabricate and use arrays of other biopolymers, polymers, or other moieties on surfaces in a manner analogous to those described above. Accordingly, reference to polymers can often be replaced with reference to "chemical moieties".

Various further modifications to the particular embodiments described above are, of course, possible. Accordingly, the present invention is not limited to the particular embodiments described in detail above.

What is claimed is:

1. A method of fabricating an array of multiple probes bonded to a front surface of a substrate at different features of the array, which substrate includes a metal layer, the method comprising:
   (a) providing the substrate wherein the front surface displays first functional groups;
   (b) contacting the front surface with linker molecules each having:
      i) a group which binds the linker molecule to the front surface following a reaction with a surface displayed first functional group, which reaction does not produce a reagent which attacks the metal layer; and
      ii) a second functional group that can be converted to a hydroxyl group wherein the second functional group is a carboxylic ester functional group,
   c) converting second functional groups on said front surface to hydroxyl groups; and
   d) contacting the front surface with the probes or probe precursors to bind the probes or probe precursors to the front surface bound linker molecules and produce the array.

2. A method according to claim 1 wherein the reaction does not produce an acid.

3. A method of fabricating an array of multiple probes bonded to a front surface of a substrate at different features of the array, which substrate includes a metal layer, the method comprising:
   (a) providing the substrate wherein the front surface displays first hydroxyl groups;
   (b) contacting the front surface with linker molecules each having:
      i) a siyloxy group which binds the linker molecule to the front surface through an ether linkage following reaction with a surface displayed hydroxyl group, and
      ii) a second functional group that can be converted to a hydroxyl group wherein the second functional group is a carboxylic ester functional group,
   c) converting second functional groups on said front surface to hydroxyl groups; and
   d) contacting the front surface with the probes or probe precursors to bind the probes or probe precursors to the front surface bound linker molecules and produce the array.

4. A method according to claim 3 wherein the probes are produced on the front surface by in situ synthesis comprising repeatedly contacting each of multiple different feature locations with probe precursors.

5. A method according to claim 3 wherein the substrate comprises a back layer, a front layer on which the front surface is located, and a metal layer positioned between the back layer and front layers.

6. A method according to claim 5 wherein the front layer comprises glass.

7. A method according to claim 5 wherein (c) comprises subjecting the front surface to alkaline conditions.

8. The method according to claim 3, wherein the probes are polymers.

9. The method according to claim 8, wherein the polymers are nucleic acids.

10. The method according to claim 8, wherein the polymers are peptides.

11. The method according to claim 3 wherein the metal layer comprises chromium.

12. The method according to claim 3, wherein the silyloxy group is a silyl alkoxide.

13. The method according to claim 12, wherein the silyl alkoxide is an ethoxide.

14. A method according to claim 3, additionally comprising converting a linker functional group to a probe or probe precursor reactive functional groups where the probe or probe precursor in (d) does not bind to the surface bound linker molecules following contact.

15. A method according to claim 3 wherein the substrate comprises a back layer, a transparent front layer on which the front surface is located, and a metal layer positioned between the back layer and front layers.

16. A method of producing a front surface modified substrate, which substrate includes a metal layer, the method comprising:
   (a) providing the substrate wherein the front surface displays first functional groups;
   (b) contacting the front surface with linker molecules each having:
      i) a group which binds the linker molecule to the front surface following a reaction with a surface displayed first functional group, which reaction does not produce a reagent which attacks the metal layer; and
      ii) a second functional group that can be converted to a hydroxyl group wherein the second functional group is a carboxylic ester functional group,
   c) converting second functional groups on said front surface to hydroxyl groups.

17. A method according to claim 16 wherein the reaction does not produce an acid.

18. A method of producing a front surface modified substrate, which substrate includes a metal layer, the method comprising:
   (a) providing the substrate wherein the front surface displays first hydroxyl groups;
   (b) contacting the front surface with linker molecules each having:

i) a siyloxy group which binds the linker molecule to the front surface through an ether linkage following reaction with a surface displayed hydroxyl group, and ii) a second functional group that can be converted to a hydroxyl group wherein the second functional group is a carboxylic ester functional group, c) converting second functional groups on said front surface to hydroxyl groups; and d) contacting the front surface with the probes or probe precursors to bind the probes or probe precursors to the front surface bound linker molecules and produce the array.

19. A method according to claim 18 wherein the substrate comprises a back layer, a front layer on which the front surface is located, and a metal layer positioned between the back layer and front layers.

20. A method according to claim 19 wherein the front layer comprises glass.

21. The method according to claim 18 wherein the metal layer comprises chromium.

22. The method according to claim 1, wherein said second functional group produces a hydroxyl group upon exposure to hydrolysis conditions.

* * * * *

UNITED STATES PATENT AND TRADEMARK OFFICE
CERTIFICATE OF CORRECTION

| | | |
|---|---|---|
| PATENT NO. | : 7,129,046 B2 | Page 1 of 1 |
| APPLICATION NO. | : 10/277925 | |
| DATED | : October 31, 2006 | |
| INVENTOR(S) | : Hargreaves | |

It is certified that error appears in the above-identified patent and that said Letters Patent is hereby corrected as shown below:

In column 15, line 61, in Claim 3, delete "siyloxy" and insert -- silyloxy --, therefor.

In column 17, line 1, in Claim 18, delete "siyloxy" and insert -- silyloxy --, therefor.

Signed and Sealed this

Tenth Day of April, 2007

JON W. DUDAS
*Director of the United States Patent and Trademark Office*